(12) United States Patent
Fichman et al.

(10) Patent No.: US 11,433,261 B2
(45) Date of Patent: Sep. 6, 2022

(54) PARTICLE FILTER MASK

(71) Applicants: PREVENTECH LTD., Lapid (IL);
DEA R&D LTD., Jerusalem (IL)

(72) Inventors: Reuven Fichman,
Makabim-Reut-Modiin (IL); Eliahu Uri Groomi Cohen, Jerusalem (IL); Ariel Pinhas Ben-Rey, Jerusalem (IL); Guy David Robin, Lapid (IL); Moran Bodas, Petach-Tikva (IL)

(73) Assignees: PREVENTECH LTD., Jerusalem (IL);
DEA R&D LTD., Jerusalem (IL)

( * ) Notice: Subject to any disclaimer, the term of this patent is extended or adjusted under 35 U.S.C. 154(b) by 616 days.

(21) Appl. No.: 14/897,998

(22) PCT Filed: Jun. 10, 2014

(86) PCT No.: PCT/IL2014/050524
§ 371 (c)(1),
(2) Date: Dec. 11, 2015

(87) PCT Pub. No.: WO2014/199378
PCT Pub. Date: Dec. 18, 2014

(65) Prior Publication Data
US 2016/0114197 A1    Apr. 28, 2016

Related U.S. Application Data

(60) Provisional application No. 61/833,485, filed on Jun. 11, 2013.

(51) Int. Cl.
*A61B 19/00*   (2006.01)
*A62B 9/06*    (2006.01)
(Continued)

(52) U.S. Cl.
CPC ............ *A62B 9/06* (2013.01); *A41D 13/1115* (2013.01); *A41D 13/1161* (2013.01);
(Continued)

(58) Field of Classification Search
CPC .............. A61M 16/0622; A61M 16/06; A61M 16/0605; A61M 16/0616; A62B 23/00;
(Continued)

(56) References Cited

U.S. PATENT DOCUMENTS 4,037,593 A   7/1977   Tate, Jr.
4,319,567 A   3/1982   Magidson
(Continued)

FOREIGN PATENT DOCUMENTS

AU   2010224323   4/2011
CN      1119549   4/1996
(Continued)

OTHER PUBLICATIONS

International Search Report for PCT/IL2014/050524, dated Oct. 9, 2014, 2 pages.
(Continued)

*Primary Examiner* — Victoria Hicks Fisher
(74) *Attorney, Agent, or Firm* — Nixon & Vanderhye PC

(57) ABSTRACT

The present invention relates to a face mask comprising (a) a mask body portion configured to surround the mouth and at least part of the nose of a wearer; (b) a sealed compressible cushion formed on the inner face of said mask body portion wherein the middle of said cushion is placed in close proximity to the middle of the superior perimeter of said mask body portion, and wherein said cushion is at least partially filled with a fluid.

13 Claims, 19 Drawing Sheets

(51) Int. Cl.
 *A62B 18/08* (2006.01)
 *A41D 13/11* (2006.01)
 *A61M 16/06* (2006.01)

(52) U.S. Cl.
 CPC ......... *A61M 16/0622* (2014.02); *A62B 18/08* (2013.01); *A41D 13/1176* (2013.01)

(58) Field of Classification Search
 CPC ....... A62B 23/02; A62B 23/025; A62B 18/08; A62B 9/06; A41D 13/11; A41D 13/1115; A41D 13/1107; A41D 13/1161; A41D 13/1138; A41D 13/1146; A41D 13/1176; A61F 13/122; A61F 13/12; A61F 13/126; A61F 13/124; A61F 5/32; A61F 5/34; A61F 5/30; A61F 5/05816; A61F 2007/0006
 USPC .......................................................... 128/863
 See application file for complete search history.

(56) References Cited

U.S. PATENT DOCUMENTS

| | | | |
|---|---|---|---|
| 4,384,577 | A | 5/1983 | Huber et al. |
| 4,641,645 | A | 2/1987 | Tayebi |
| 5,181,506 | A | 1/1993 | Tardiff, Jr. et al. |
| 5,727,544 | A * | 3/1998 | Miura .................... A41D 13/11 128/201.13 |
| 5,921,239 | A | 7/1999 | McCall et al. |
| 6,092,521 | A | 7/2000 | Miura |
| 6,615,832 | B1 | 9/2003 | Chen |
| 6,644,314 | B1 * | 11/2003 | Elsberg .................. A41D 13/11 128/205.27 |
| 7,107,989 | B2 | 9/2006 | Frater et al. |
| 7,523,754 | B2 | 4/2009 | Lithgow et al. |
| 2005/0187502 | A1* | 8/2005 | Krempel .................. A61F 7/02 602/5 |
| 2006/0118117 | A1 | 6/2006 | Berthon-Jones et al. |
| 2006/0283454 | A1 | 12/2006 | Delaney et al. |
| 2008/0099022 | A1* | 5/2008 | Gebrewold ........ A41D 13/1138 128/206.21 |
| 2010/0154805 | A1 | 6/2010 | Duffy et al. |
| 2011/0094515 | A1 | 4/2011 | Duffy |
| 2012/0060843 | A1 | 3/2012 | Magidson et al. |
| 2012/0097167 | A1 | 4/2012 | Ono et al. |
| 2012/0272973 | A1* | 11/2012 | Palomo .............. A41D 13/1115 128/863 |
| 2015/0040920 | A1* | 2/2015 | Spanner .................... B32B 5/00 128/863 |

FOREIGN PATENT DOCUMENTS

| | | |
|---|---|---|
| CN | 2390626 | 8/2000 |
| CN | 2592201 | 12/2003 |
| CN | 1735439 | 2/2006 |
| CN | 101829413 | 9/2010 |
| CN | 102019051 | 4/2011 |
| EP | 1 495 785 | 1/2005 |
| EP | 2 298 096 | 3/2011 |
| GB | 1 467 828 | 3/1977 |
| JP | 50-689 | 1/1975 |
| JP | 2003-741 | 1/2003 |
| JP | 2003-305133 | 10/2003 |
| JP | 2005-529687 | 10/2005 |
| JP | 2006-505373 | 2/2006 |
| JP | 2006-130256 | 5/2006 |
| JP | 2009-66382 | 4/2009 |
| JP | 4481650 | 6/2010 |
| JP | 2011-10902 | 1/2011 |
| JP | 2011-92698 | 5/2011 |
| JP | 2013-48898 | 3/2013 |
| KR | 20-1999-0040778 | 12/1999 |
| KR | 10-2009-0109815 | 10/2009 |
| RU | 2010 138 662 | 3/2012 |
| WO | WO 86/01734 | 3/1986 |
| WO | WO 2004/041342 | 5/2004 |
| WO | WO 2013/056389 | 4/2013 |

OTHER PUBLICATIONS

Written Opinion of the ISA for PCT/IL2014/050524, dated Oct. 9, 2014, 5 pages.
Partial European Search Report issued in App. No. 14810564.6 dated Dec. 19, 2016.
Extended European Search Report issued in Appln No. 14810564.6 dated Apr. 3, 2017.
Office Action issued in JP Appln. No. 2016-518643 dated Jul. 17, 2018 (w/ translation).
Office Action issued in CN Appln. No. 201480043714.9 dated Jun. 4, 2018 (w/ translation).
Notice of Decision of Rejection dated Jun. 24, 2021 in corresponding Korean Application No. 10-2015-7035084, 4 pages.
Office Action dated Sep. 27, 2021 in Korean Application No. 10-2015-7035084 (with translation), 16 pages.
Office Action issued in KR Appln. No. 10-2015-7035084 dated Dec. 18, 2020 (w/ translation).

* cited by examiner

FIG. 2A
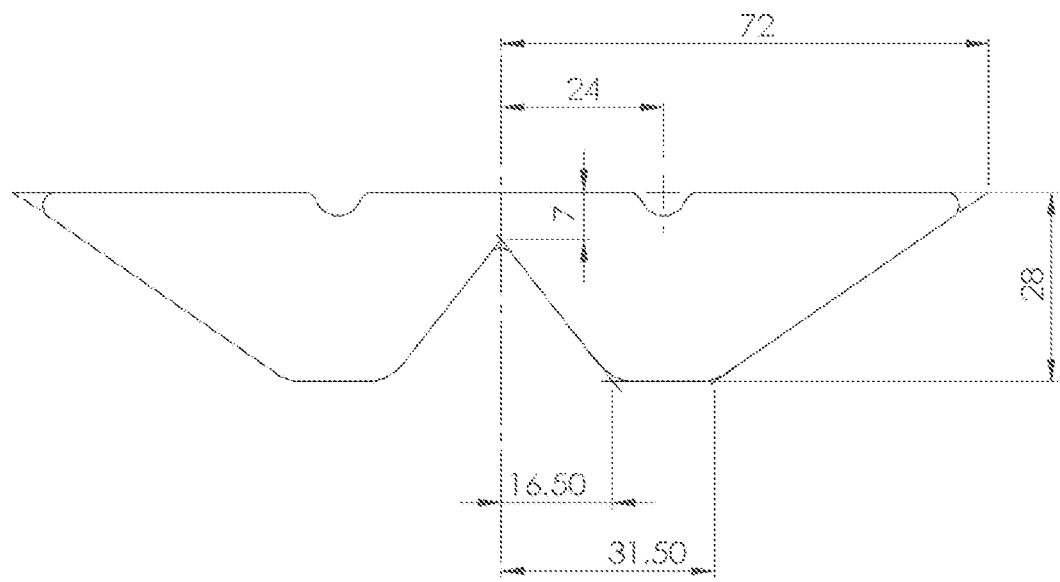
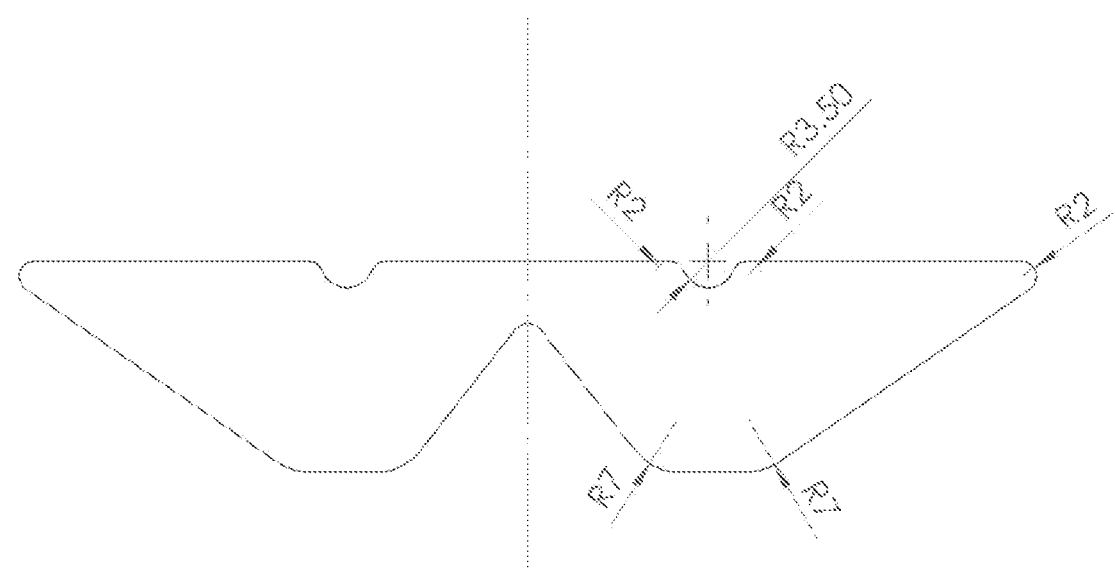

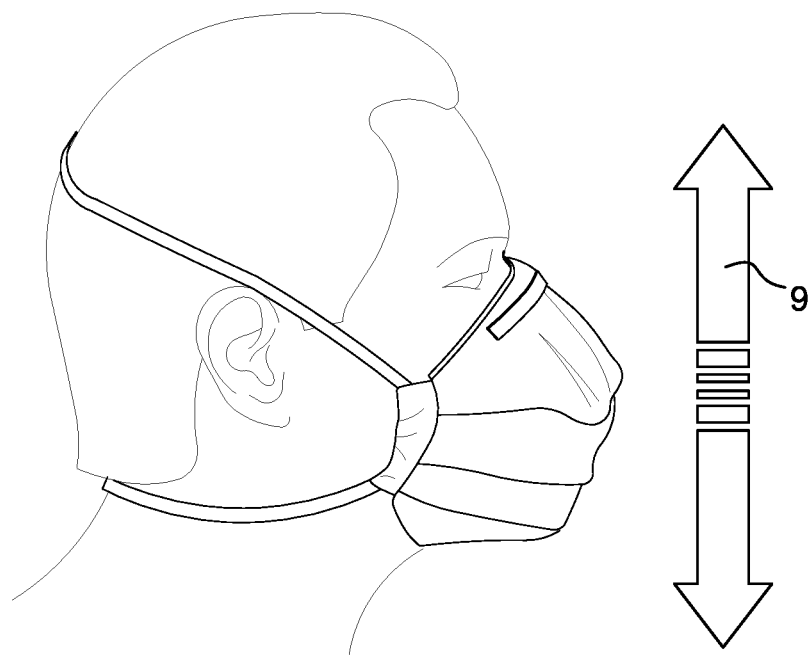
FIG. 6
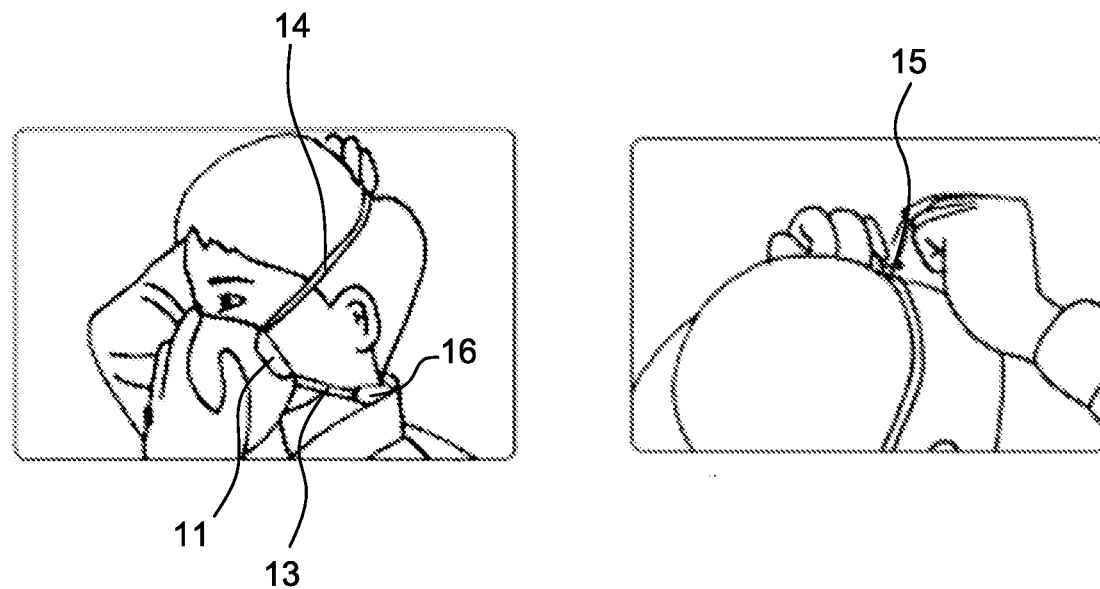
FIG. 7a  FIG. 7b

FIG. 10

| Mask | | Subject 1 (NIOSH Sec. 1) | Subject 2 (NIOSH Sec. 1) | Subject 3 (NIOSH Sec. 3) | Subject 4 (NIOSH Sec. 4) | Subject 5 (NIOSH Sec. 3) |
|---|---|---|---|---|---|---|
| Present invention models (w/ cushion) | Flat-cut | 181 | 181 | 157 | 187 | 136 |
| | Pleats | 466 | 738 | 401 | 798 | 448 |
| Prior Art | 1 | 43 | 199 | 8.4 | 67 | 103 |
| | 2 | 22 | 58 | 55 | 7.2 | 95 |
| | 3 | 4.2 | 18 | 6.1 | - | - |

Protection Factor (FIT factor) results obtained with PORTACOUNT Pro Plus 8038

(threshold "pass" criteria according to OSHA 29 CFR1910.134 is FIT Factor ≥ 100)

FIG. 11
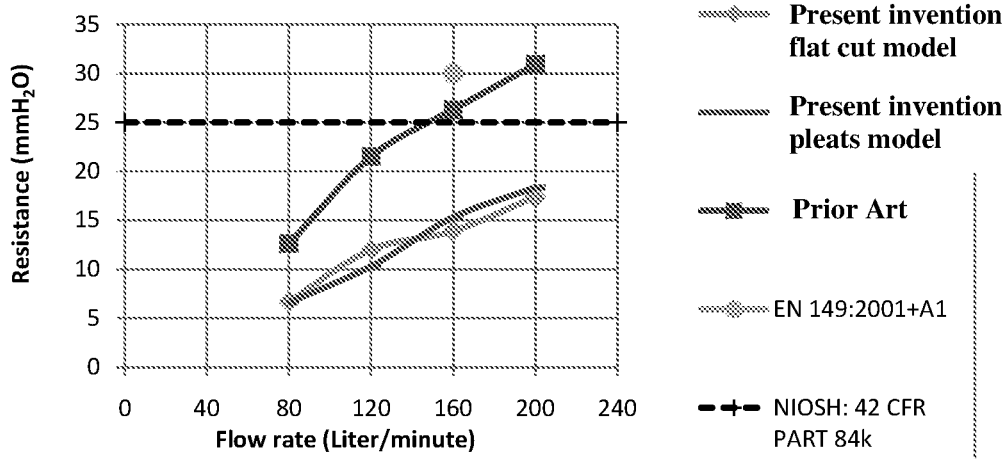
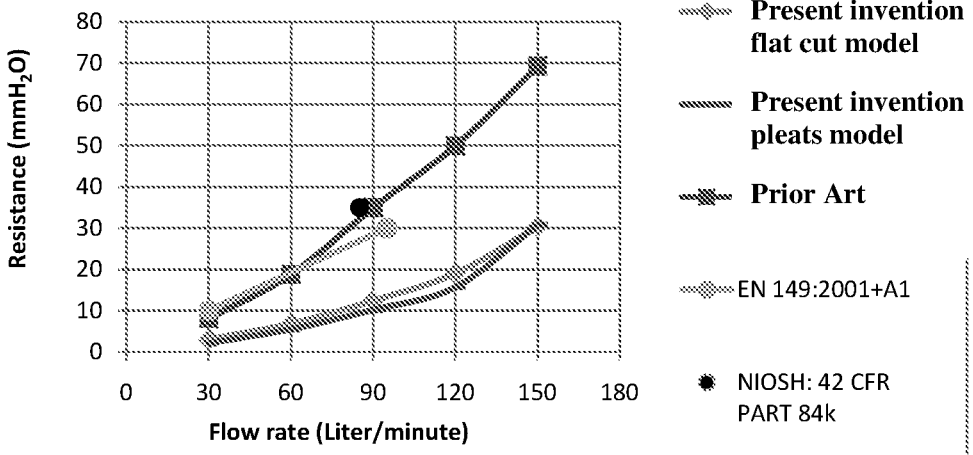

PARTICLE FILTER MASK

This application is the U.S. national phase of International Application No. PCT/IL2014/050524 filed 10 Jun. 2014, which designated the U.S. and claims the benefit of U.S. Provisional Application No. 61/833,485 filed 11 Jun. 2013, the entire contents of each of which are hereby incorporated by reference.

FIELD OF THE INVENTION

The present invention relates to the field of disposable masks for personal protection. More particularly, the present invention relates to a disposable mask capable of filtering microscopic particles from penetrating therethrough.

BACKGROUND OF THE INVENTION

The use of disposable masks for personal protection is well known in the art. In many cases—for example masks used to protect workers in industrial environments such as workshops or factories in which wood, metal and/or polymeric materials are processed—the masks are used in order to prevent staff from inhaling potentially harmful particulate matter such as dust, sawdust, shavings, etc. In such cases, it is often sufficient for the masks to relatively loosely cover the mouth and nostrils and allow filtration levels around 95-99%.

In other cases, however, it is of vital importance for the mask to be completely sealed around its perimeter to the user's face, in order to prevent the ingress of microscopic particulate matter, for example radioactive particles, and/or pathogenic agents such as bacteria or viruses. These kinds of particulate matter, in particular pathogenic agents, spread in the air in the form of microscopic particle clouds and therefore it is vital that the mask will be sealed around the whole peripheral area of the mask to prevent penetration of such particles.

Masks of this type are of particular importance to both the medical and defense establishments—in the former for preventing the person-to-person spread of pathogenic organisms and in the latter, for example, to protect users from the potentially lethal effects of biological weapons deployed during times of war and in terrorist attacks. Masks of this type are also useful for safety and industrial applications.

In order to efficiently protect the user against harmful biological agents carried in particles of 0.3 micron or more, the mask must possess at least the following two essential properties:

a) Adequate sealing around the entire perimeter of the mask to the face of the user, such that at least the nose and mouth are completely enclosed, thereby preventing the ingress of harmful agents under said perimeter. In particular, the mask must be capable of providing an air-tight seal with a high fit factor around its perimeter when applied to the face of any user, regardless of individual anthropometric differences. The efficient sealing should be during all operating conditions, for example while talking, in order to ensure that air exchange between the inner and outer parts of the mask is conduct solely through the filtration medium.

b) Permit the user to breathe with minimal interference, despite the fact that both the nostrils and the mouth are entirely enclosed by the mask.

The need for a new particle filtration mask is due to several findings indicating that prior art devices have generally been found deficient with regard to the first property, namely perimeter sealing. In many prior art masks, a vulnerable area with a potential lack of sealing and where air leakage can occur is between the bridge of the nose and the top portion of the cheek bone. That curved area makes it difficult to seal. Also, a great deal of discomfort can be caused to a user with glasses, since the air leaking out of said area flows upwards and steams up the glasses.

One example of a prior art solution is described in US 2011/0094515 which describes a respirator that has a harness and a mask body that is joined to the harness. The mask body includes a filtering structure that may contain a plurality of layers of nonwoven fibrous material. The layers of nonwoven fibrous material have a thickness A and are welded together by at least two parallel weld lines that are spaced at 0.5 to 6 times A.

US 2010/0154805 discloses a flat-fold, filtering facepiece respirator for being worn over breathing passage of person. It has a mask body comprising a filtering structure and flanges positioned on sides of mask body and projected from mask body.

US 20120097167 relates to a mask with a nosal cushion, the mask consisting of a filter that filters dust, wherein, the edges of the filter are folded back to create flaps that follow the depressions on both sides of the nosal region. A sponge of urethane foam or the like is affixed inside the flaps, thereby improving the fit of the mask by conforming the mask to the contours of the nosal region, resulting in a mask cushion with a nosal cushion.

U.S. Pat. No. 4,037,593 relates to a surgical mask with a vapor barrier for preventing clouding or fogging of optical aids or devices used by the wearer of the mask. The vapor barrier comprises a contoured strip of elongated soft closed cell foam material interposed between the upper edge of the mask and the wearer's face.

U.S. Pat. No. 4,384,577 relates to face mask for filtering air to a wearer including a plurality of non-woven fibers molded in a generally cup shaped configuration for fitting over the mouth and nose of the wearer and with the cup shaped configuration including a nose bridge portion for lying along the bridge of the nose of the wearer, nose pad portions aligned to either side of the nose bridge portion for fitting against the sides of the nose and a central portion lying below the nose bridge and nose pad portions.

U.S. Pat. No. 4,641,645 relates to a face mask formed from a porous sheet made of a plurality of fibers. The mask is formed into a generally cup shape shell that fits over the mouth and nose of the wearer and is held thereto by elastic straps attached to the mask that pass behind the head when the mask is worn. The mask filters breathed air passing through the mask. The border of the mask is more tightly compacted during forming. The mask of the present invention features rearwardly projecting portions located on either side of the nose bridge area of the mask parallel to and close to the border of the mask.

U.S. Pat. No. 4,319,567 relates to a face mask formed by a plurality of fibers and generally having a cup shape to fit over the mouth and nose of a wearer and for filtering the air passing through the fibers, including, a nose bridge portion, nose pad portions to either side of the nose bridge portion to fit against the sides of the nose and against the cheekbones of the wearer, and a central portion of the face mask below the nose bridge portion and the nose pad portions.

However none of the prior art methods disclose masks that can provide a full effective perimeter sealing and for a variety of face sizes. A pressing need for the provision of a disposable face mask having improved perimeter sealing properties thus exists. It is the aim of the present invention to fulfill this need.

It is therefore an object of the present invention to provide means for safe breathing and effective sealing of a mask to the face enabling same.

Other objects and advantages of the present invention will become apparent as the description proceeds.

SUMMARY OF THE INVENTION

The present invention relates to a mask with high filtration capabilities, for preventing the passage of, inter alia, biological agents. The mask comprises a structure that enables the easy application of the mask to the face and comfortable use for prolonged periods of time. The mask enables easy breathing therethrough with low breathing resistance. The mask provides complete sealing around the peripheral edge of the mask body. The present invention mask enables a user to speak and make facial movements without breaking said sealing of the mask. The present invention mask enables a maximal field of vision and its use is compatible with eye-glasses and other medical instruments.

The present invention relates to a mask comprising cushions at one or more areas at the edge of the mask body to provide additional sealing support for areas which are prone to sealing/air breakthroughs. The present invention mask is adapted to fit on various faces having different sizes or facial structures, providing an effective sealing regardless of the size or facial structure of the user.

The present invention relates to a face mask comprising:
(a) a mask body portion configured to surround the mouth and at least part of the nose of a wearer;
(b) a sealed compressible cushion formed on the inner face of said mask body portion wherein the middle portion of said cushion is placed in close proximity to the middle portion of the superior perimeter of said mask body portion, and wherein said cushion is at least partially filled with a fluid.

Preferably, the cushion is comprised of two EVA (Ethylene-vinyl acetate) films or comprised of Polyethylene (PE) films or of a laminate comprising Polyethylene (PE).

Preferably, the cushion is attached to the mask body portion and wherein the middle portion of said cushion is attached at close proximity to the middle of the superior perimeter of said mask body portion.

Preferably, the mask body portion further comprises a holding element attached to the inner face of said mask body portion at close proximity to the middle portion of the superior perimeter of said mask body portion;
wherein said holding element is configured to receive and hold a portion of the cushion threaded thereinto.

Preferably, the cushion is comprised of films or sheets having a shape of two adjacent polygons having a common portion in the middle portion. Preferably, the polygons are trapezoids.

Preferably, the cushion comprises two wider lateral pocket portions, wherein said lateral pocket portions have larger volumes than that of the middle portion of said cushion, wherein the middle portion is configured to fit on the bridge of the nose of a wearer, and said two lateral pocket portions are configured to be deployed on the sides of the nose of a wearer, thus being configured to seal the area between the upper cheeks and the eye sockets of a wearer.

Preferably, the cushion is partly filled with a fluid.

Preferably, the mask body portion is comprised of layers of nonwoven fabrics.

Preferably, the mask body portion comprises three functional layers.

Preferably, the mask body portion comprises a portion that is folded into a series of pleats.

Preferably, the pleats are formed along the width portion of the mask body portion and are made by folding a portion of the mask body portion into pleat layers and welding the edges together.

Preferably, the face mask further comprises a distinct second sealed compressible cushion, wherein the first sealed compressible cushion and the second sealed compressible cushion are connected to each other at the midline of the superior border of the mask body portion, and wherein said second cushion is at least partially filled with a fluid.

Preferably, the cushion further comprises a one way inflation valve.

The present invention relates to a face mask comprising:
(a) a mask body portion configured to surround the mouth and at least part of the nose of a wearer;
(b) one or more sealed compressible cushions at least partially filled with fluid, formed on the inner face of said mask body portion, wherein said one or more cushions extend over a portion of the perimeter of said mask body portion.

Preferably, the one or more cushions extend around the entire perimeter of the mask body portion.

The present invention relates to a face mask comprising:
(a) a mask body portion configured to surround the mouth and at least part of the nose of a wearer;
(b) a single adjustable elastic strap threaded into two threading channels, each threading channel located on the sides of the mask body portion;
(c) a tightening buckle wherein the edges of said elastic strap are passed therethrough, wherein said buckle is configured to hold said strap at a required length.

Preferably, the face mask further comprises a sealed compressible cushion filled with fluid formed on the inner face of said mask body portion wherein the middle of said cushion is placed at close proximity to the middle of the superior perimeter of said mask body portion.

Preferably, the strap is made of a material selected from the group consisting of Polyester, Lycra and rubber.

Preferably, the face mask further comprises grip tabs attached to the threading channels.

Preferably, each threading channel and grip tab are made by plastic injection wherein said threading channels are welded to the side edges of the mask.

Preferably, each threading channel and grip tab are made of a nonwoven fabric.

Preferably, each threading channel and grip tab are made of the same material as the mask body portion, and is an integral part of said mask body portion.

Preferably, the threading channels and grip tabs are welded to be stiffened and hardened.

BRIEF DESCRIPTION OF THE DRAWINGS

The present invention is illustrated by way of example in the accompanying drawings, in which similar references consistently indicate similar elements and in which:

FIGS. 2A and 2B illustrate embodiments of the cushion of the present invention.

FIG. 6 illustrates an embodiment of the mask with pleats.

FIGS. 7a-7b illustrate an embodiment of the single strap mask.

FIG. 10 illustrates a table of the test results of an experiment.

FIG. 11 illustrates a graph of the test results of an experiment.

DETAILED DESCRIPTION OF THE INVENTION

The present invention is primarily directed to a face mask, having the ability to provide a tight seal around its perimeter on the facial skin of the wearer. As said, in many prior art masks, a vulnerable area with a potential lack of sealing and where air leakage can occur is between the bridge of the nose and the top portion of the cheek bone. That curved area has a complex morphological structure which makes it difficult to seal.

Figure 1:
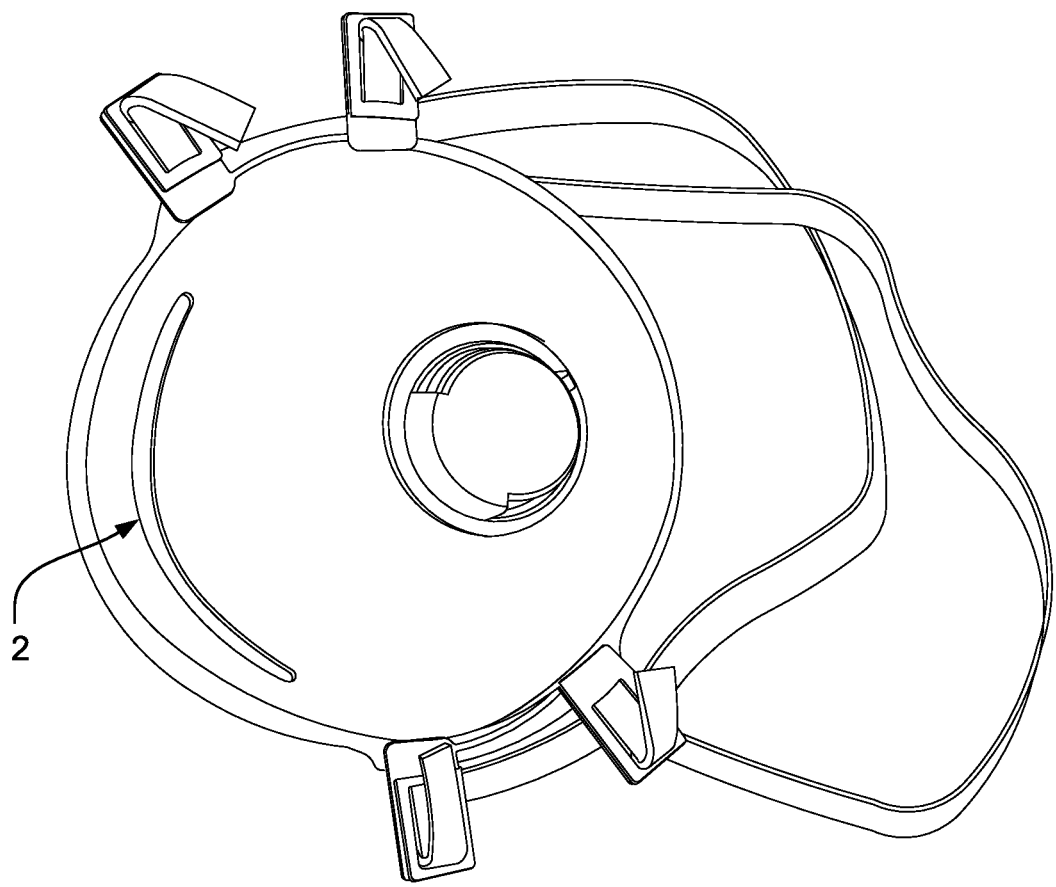
FIG. 1 illustrates a prior art mask.

To solve this problem many prior art masks use a flexible aluminum strip 2 pressed on the upper bridge part of the nose and down its sides, as shown in FIG. 1. The flexible aluminum strip is used in combination with soft material on the skin. Other prior art masks are designed to tightly embrace the upper nose portion (i.e. nose bridge and Maxilla areas). These prior art masks do not provide sufficient solutions. The prior art masks are not efficient for usage with faces of various dimensions and shapes, wherein the effectiveness of the sealing varies accordingly.

The present invention face mask comprises one or more sealed compressible pouches or cushions (used herein interchangeably) located around at least a portion of the perimeter thereof. The purpose of said compressible pouch or pouches is to permit at least the portion of the perimeter of the mask that comes into contact with the bridge and upper lateral portions of the nose to be readily adaptable to those structures, regardless of the actual facial shape and dimensions of the user. The compressible pouches compensate for the non-sealed areas, when the mask is applied, being efficiently adapted to the facial structure causing a most effective seal therein. In this way, the perimeter of the mask may be completely sealed around the user's face.

The face mask comprises a mask body portion configured to surround the mouth and at least part of the nose of a wearer. The mask further comprises a sealed compressible cushion formed on the inner face of the mask body portion wherein the middle of the cushion is placed in close proximity to the middle of the superior perimeter of the mask body portion, and wherein the cushion is at least partially filled with a fluid.

In one preferred embodiment of this aspect of the invention, the at least one sealed compressible pouch is provided in the form of one or more air-filled cushions. In other embodiments, the compressible pouches are filled with fluid or liquid gel or water or silicon crystals. In a preferable embodiment the pouches are filled with air. In still further embodiments, these pouches may contain other solid, gaseous or liquid filling materials or a mixture thereof.

In one particularly preferred embodiment, the compressible pouch may be formed on the medial portion of the superior (upper) portion of the perimeter of the mask, such that when fitted to the user's face, said pouch is brought into contact with the bridge of the nose and the skin overlying the portions of the maxilla on either side of the nose. Accordingly, the pouch is attached to the inner side of the mask body portion, i.e. the proximal side that is configured to be in contact with the user's face (as opposed to the outer (distal) side, farther from the user's face).

In one preferred embodiment of this type, a single pouch passes from the region of the left side of the nose, over the bridge, to the right side of the nose. In other preferred embodiments, this embodiment is implemented by means of two distinct pouches connected to each other at the midline of the superior border of the mask.

According to one embodiment, the mask comprises a single cushion comprised of two EVA films (or sheets), each with a thickness usually between 50-200 microns (preferably 110 microns). According to another embodiment the cushion is comprised of Polyethylene (PE) films (or sheets) or of a laminate comprising Polyethylene (PE), having a thickness usually between 40-180 microns, preferably 100 microns.

Figure 5A:
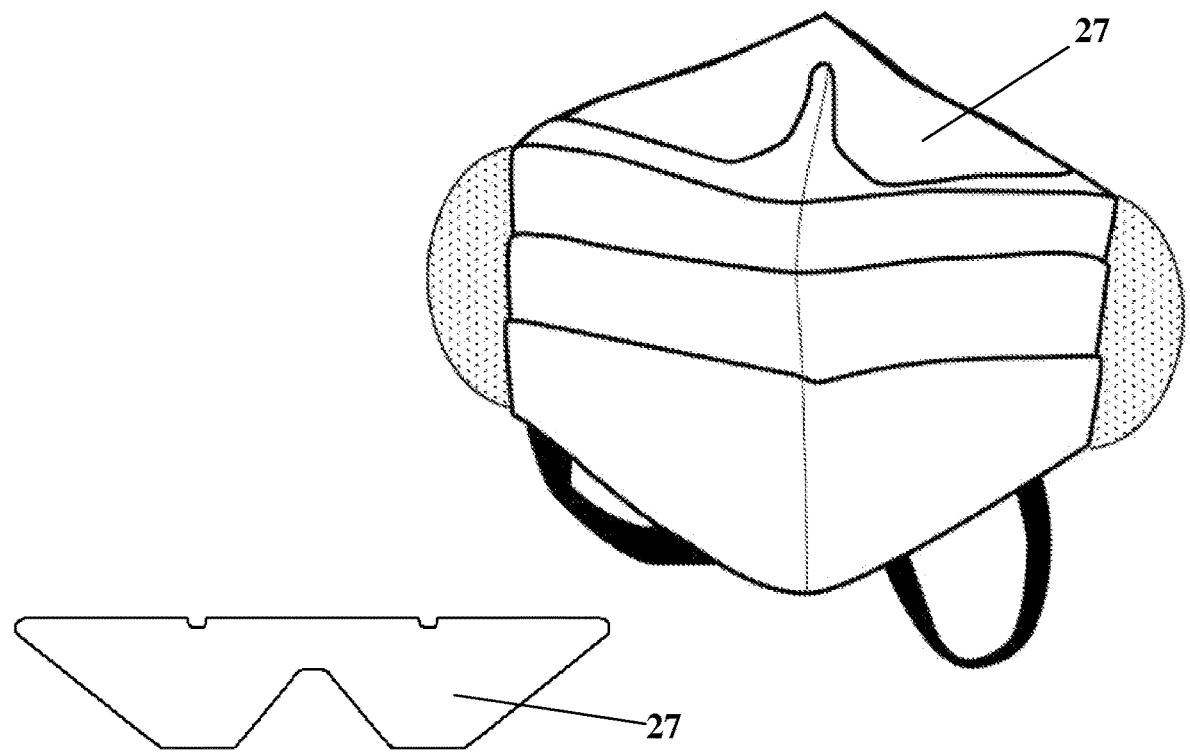
FIG. 5A illustrates an embodiment of the mask with the cushion.
Figure 5B:
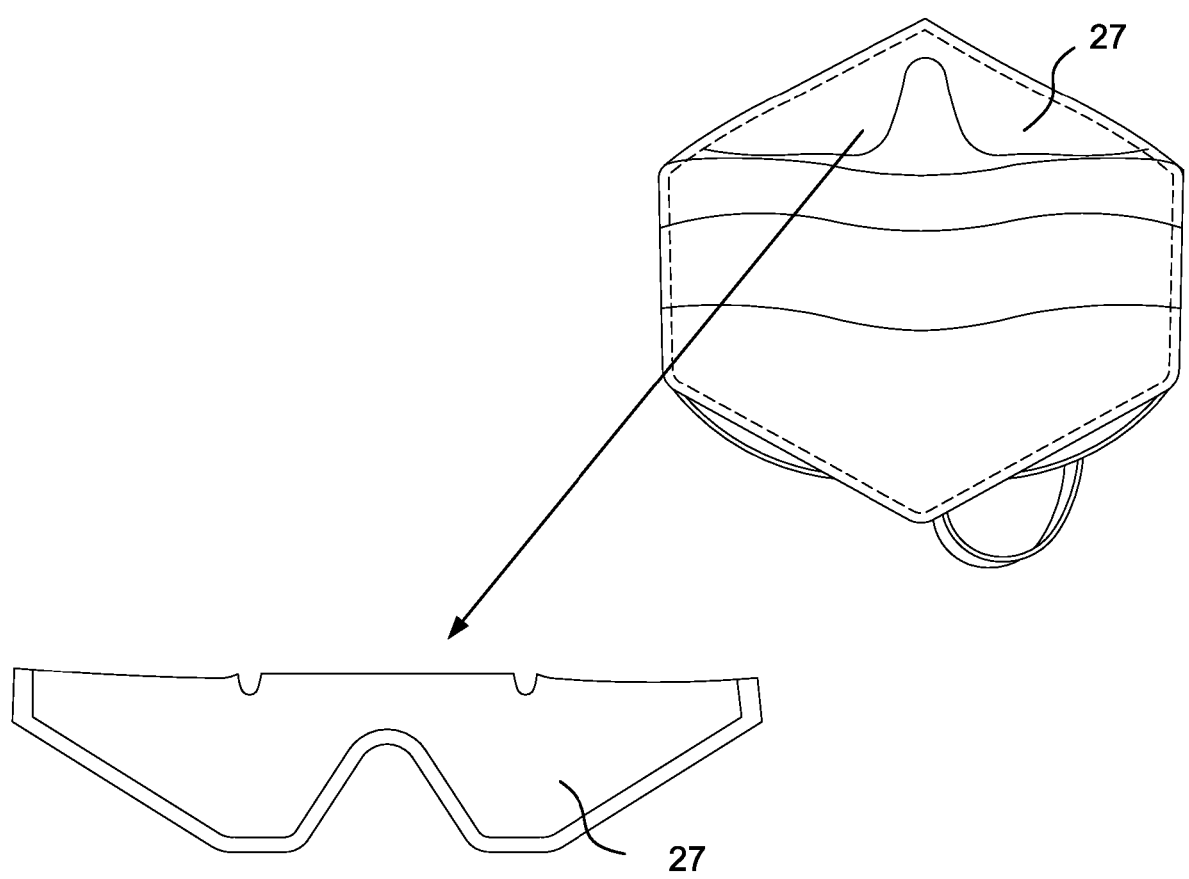
FIG. 5B illustrates a pictorial example of FIG. 5A.

The construction of the cushion is done by welding (e.g. RF welding, ultrasonic welding) of two EVA films in a brass frame having the contour of the pouch films. Fluid e.g. air) is injected into the space between the welded films, usually filled with 5-20 cc of air, preferably 8 cc of air. The injection of the fluid is done by a syringe and then the remaining open hole portion is welded. Thus the cushion is completely sealed. The cushion is then sealably attached to the inside upper portion of the mask body. Preferably, the cushion is glued to the inside upper portion of the mask body. According to one embodiment the mask comprises a holding element 29 (as shown in FIG. 5E) such as a pocket or loop, placed at the inside upper portion of the mask adapted to receive and hold the cushion 27. Preferably, the cushion 27 is threaded in the pocket (or loop).

The films that comprise the cushion preferably have a shape of two adjacent polygons (e.g. trapezoids) having a common portion in the middle. An example of this shape comprising two adjacent trapezoids having a common portion in the middle, can be seen in FIG. 2A. Preferably, the polygon edges are straight, or with a slight convex curve facing the outside or inside of the polygon.

According to the embodiment shown in FIG. 2A, the wide upper base of each trapezoid is usually between 60 mm and 80 mm and preferably 72 mm. The lower base of each trapezoid is usually between 5 mm and 18 mm and preferably 15 mm. The height (the distance between both parallel bases) is usually between 20 mm and 35 mm and preferably 28 mm. The distance between the lower bases is usually between 26 mm and 50 mm and preferably 33 mm. The narrowest vertical portion (adapted to fit on the nose bridge) is usually between 5 mm and 10 mm and preferably 7 mm. Optionally, the wide bases each comprise a half circular aperture with a radius usually between 2.5 mm and 4.5 mm and preferably 3.5 mm. The distance between the circular apertures is usually between 40 mm and 80 mm, preferably 58 mm.

Figure 2B:
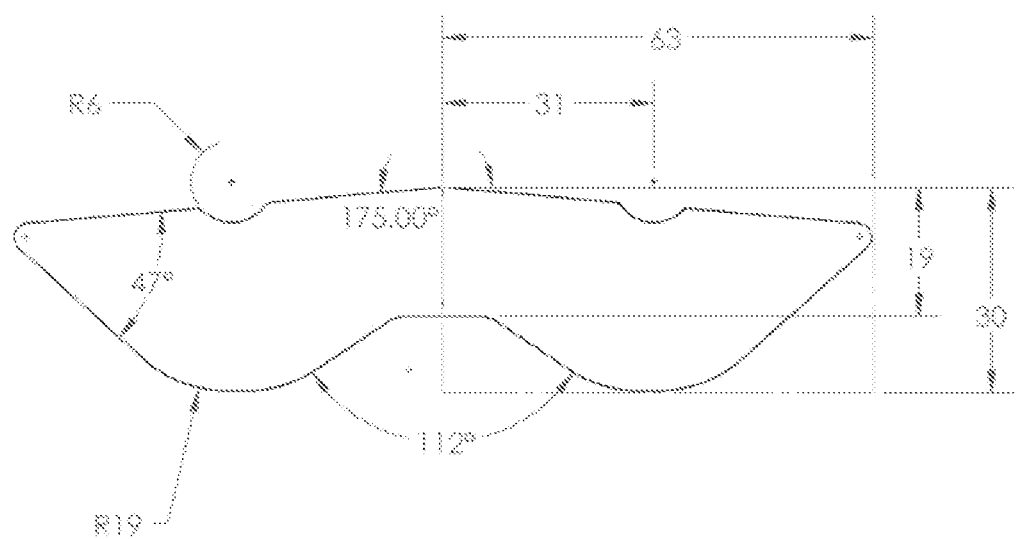

According to the embodiment shown in FIG. 2B, the cushion comprises a smaller width and part of the sides comprise an arc shape. The two trapezoids common portion in the middle forms an angle (and not straight line) usually between 150-180 degrees, preferably 175 degrees. The angle between the larger bases and the outer legs is usually between 35 to 60 degrees, preferably 47 degrees. The angle between the inner legs is usually between 60 and 180 degrees, and preferably 112 degrees. The "small bases" of the trapezoids comprise an arc shape usually with a radius between 15 to 25 mm, and preferably 19 mm. The entire length of the cushion is usually between 100 to 160 mm, preferably to 126 mm. The total cushion height is usually between 20 and 40 mm, and preferably 30 mm.

The narrowest vertical portion (adapted to fit on the nose bridge) is usually between 5 mm and 35 mm and preferably 19 mm. Optionally, the wide bases each comprise a half circular aperture with a radius usually between 1 mm and 10 mm and preferably 6 mm. the distance between the circular apertures is usually between 40 mm and 80 mm, and preferably 62 mm.

Figure 3A:
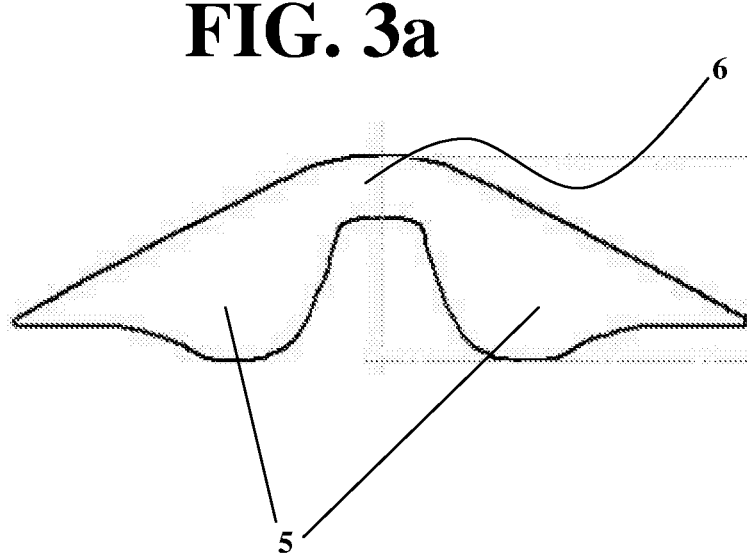
FIGS. 3a-3b illustrate an embodiment of the cushion of the present invention and an example of a location placed on the face.
Figure 3B:
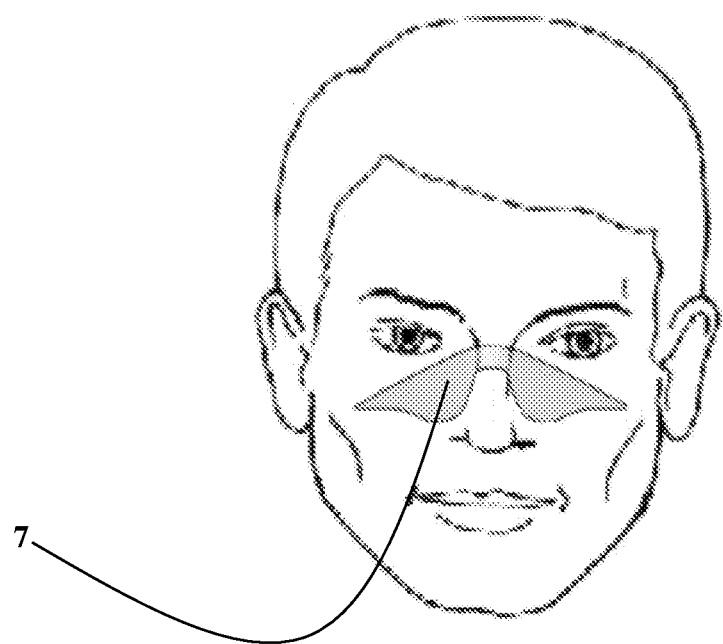

FIG. 3a shows an example of the general shape of the cushion when applied on a user. The cushions comprise two wider lateral pocket portions 5 on the sides having larger volumes than that of the middle section 6. The narrow middle section 6 is adapted to fit on the bridge of the nose. The two lateral pocket portions 5 are adapted to be deployed on the sides of the nose, thus sealing the area between the upper cheeks and the eye sockets. An example of the correct position of the cushion is demonstrated in the shaded portion 7 in FIG. 3b.

Figure 4A:
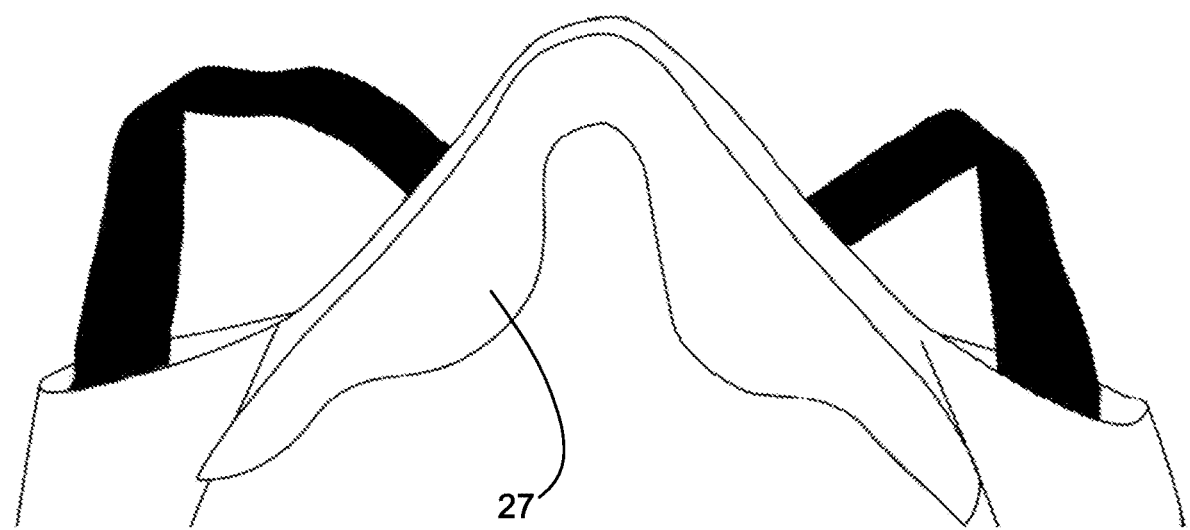
FIG. 4A illustrates an embodiment of the mask with the cushion.
Figure 4B:
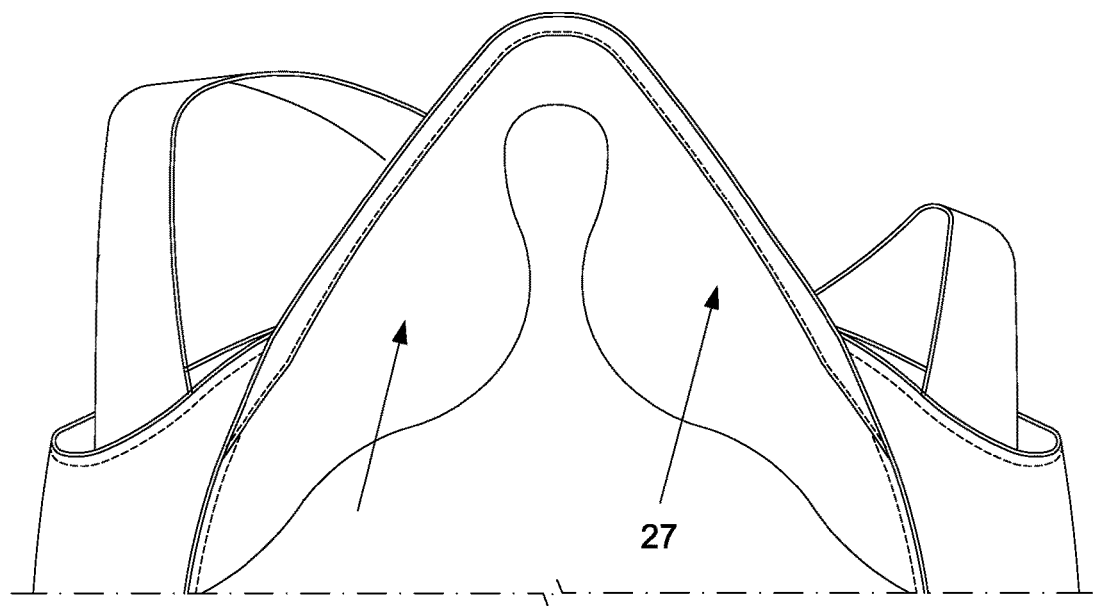
FIG. 4B illustrates a pictorial example of FIG. 4A.

FIG. 4A shows a mask comprising the inflated cushion 27. FIG. 4B is a pictorial example of FIG. 4A. FIG. 5A shows a mask comprising the cushion (with pleats as will be explained hereinafter) and also shows an enlarged illustration of the inflated cushion alone (left bottom portion). FIG. 5B is a pictorial example of FIG. 5A. The cushions also prevent an unwanted pressure applied to the nose that exist in some prior art masks. The mask with the cushions enables an efficient sealing for all types of faces regardless of their anthropometric differences, because the cushion fits itself to the facial structure of the users.

Figure 5C:
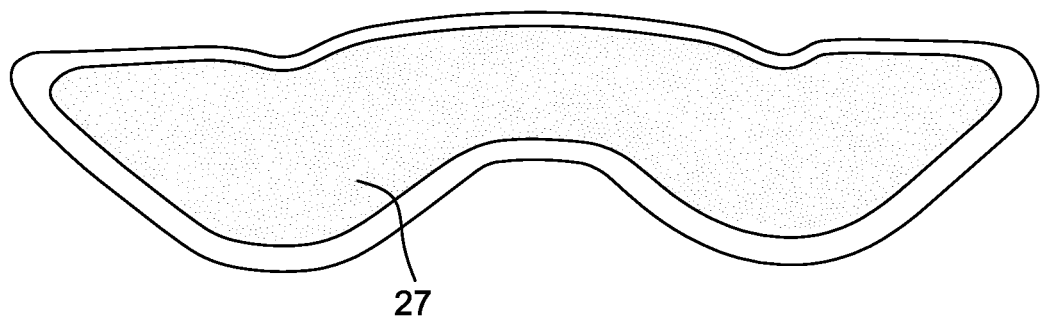
FIG. 5C is a pictorial example of a cushion filled with liquid gel.
Figure 5D:
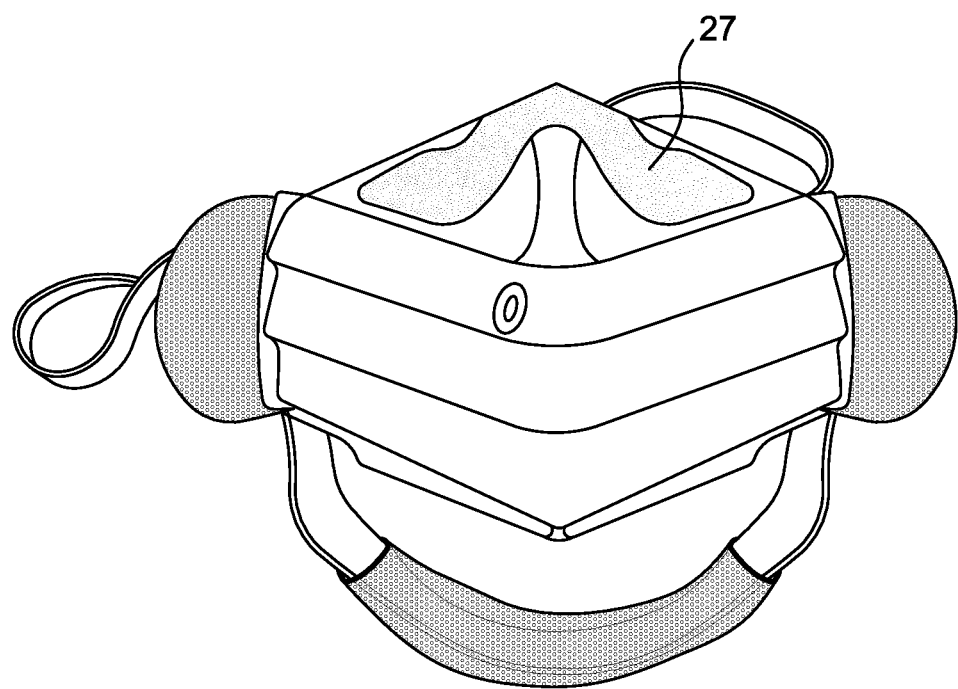
FIG. 5D is a pictorial example of an embodiment of the present invention mask comprising the cushion of FIG. 5C filled with liquid gel.
Figure 5E:
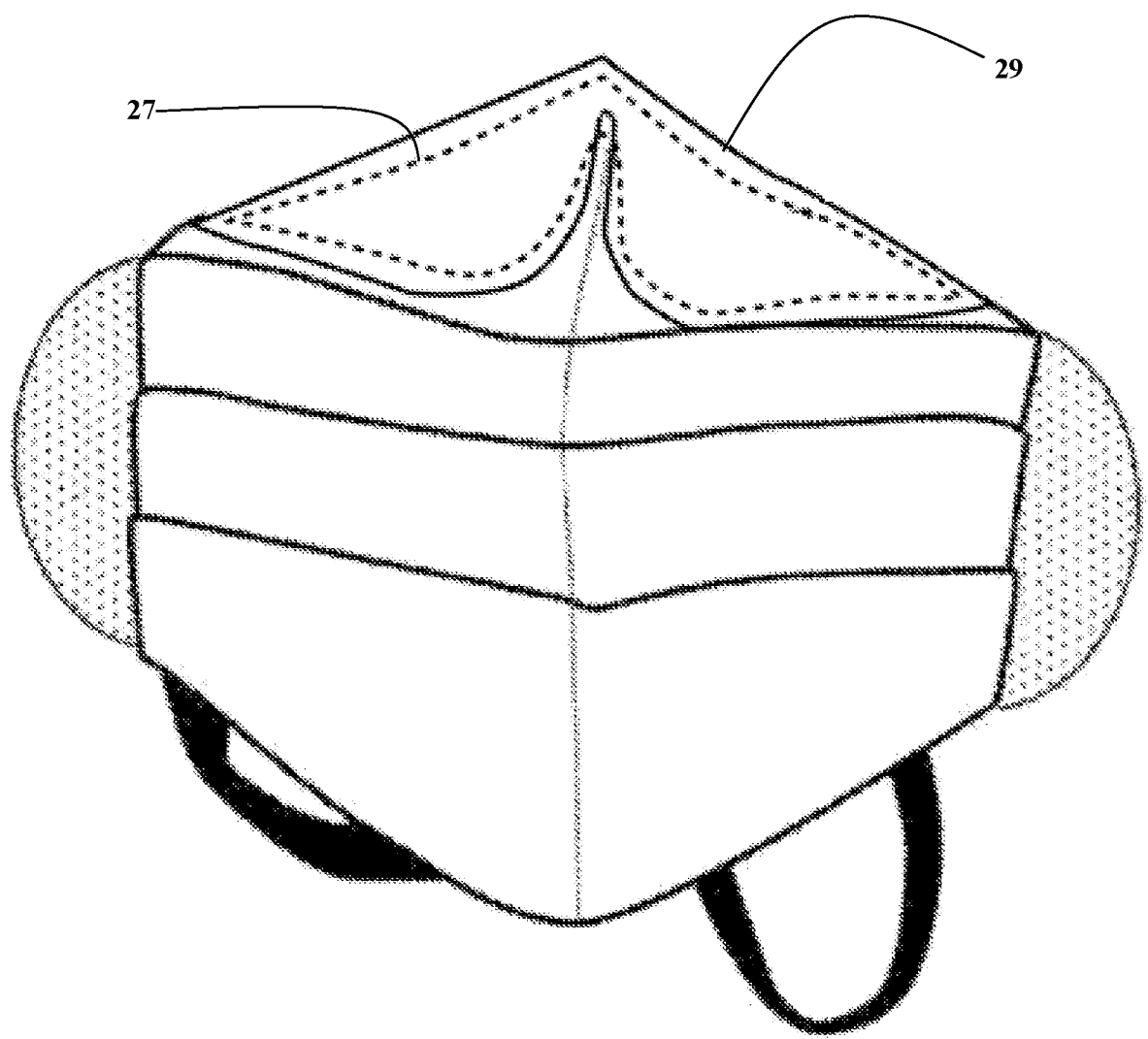
FIG. 5E illustrates holding element 29.

FIG. 5C is a pictorial example of a cushion 28 filled with liquid gel. FIG. 5D is a pictorial example of an embodiment of the present invention mask 50 comprising the cushion 28 filled with liquid gel.

According to a preferred embodiment, the cushion is only partly filled with the fluid filling, thus being flexible and adaptive to curvatures. In this manner when wearing the mask, the cushion actually adapts itself to the wearer's face in a very efficient manner. Part of the fluid can travel from one portion to another (e.g. from the left side trapezoid portion to the right side trapezoid portion) when the first portion is compressed or squeezed. This allows for the filling of any vacant space which otherwise would be a potential leaking point in the seal of the mask. This feature assists in forming a complete seal at the nose bridge and nose side areas of the mask. Accordingly, if the wearer's face is not symmetric, part of the fluid will flow from one side portion to the other until an even effect is achieved, thus obtaining an even more efficient seal on both sides.

For example, if the wearer's face comprises a protruding portion at the right side of the nose bridge, part of the fluid within the cushion side engaging that protrusion side will travel to the other side, thus resulting in a full contact of the cushion with the skin forming an even more efficient seal. The mask left side of the cushion is actually filled (causing a slight protrusion of the mask on the left side) compensating for the right side portion of the mask protruding due to the protrusion, thus receiving an even effect and a more efficient seal.

In another example, if the wearer's face comprises a hole portion at the right side of the nose bridge, part of the fluid within the cushion side opposite of that hole side will travel to the hole side compensating and filling the hole, thus resulting in a full contact of the cushion with the skin forming an even more efficient seal. The fluid traveling and compensating contributes to forming an efficient seal. The mask left side of the cushion is actually "de-filled", i.e. partly emptied, (causing a slight depression of the mask inwards towards the face on the left side) compensating for the right side portion of the mask depression inwards due to the hole, thus receiving an even effect and a more efficient seal.

Accordingly, the cushion can adapt to fit on faces of various sizes.

According to another embodiment of the invention, the cushion comprises a one way inflation valve for a user to self inflate fluid (usually air) into his own cushion, thus inflating a desirable amount of fluid until an optimal efficient sealing (or optimal comfortable sealing) is obtained. A corresponding appropriate pump is provided configured to connect to the valve for the cushion inflation. When the cushion reaches the required size, the pump is detached. Optionally the pump is positioned near the cushion and can remain near the cushion even after the inflation. Optionally, fluid can also be removed from the cushion. In a most efficient manner, the wearer can pump the required amount of fluid when wearing the mask.

Figure 12:
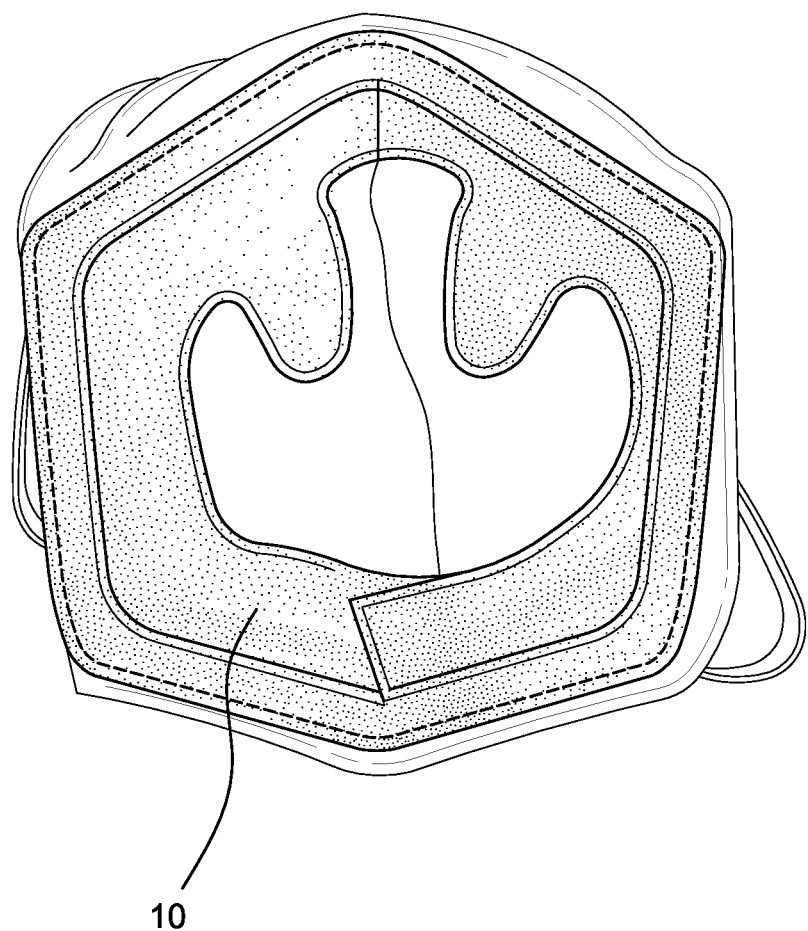
FIG. 12 illustrates an embodiment of the present invention comprising a pouch extending around the entire perimeter of the mask.

In other preferred embodiments of the invention, the mask may comprise one or more compressible pouches that extend over a greater portion of the perimeter thereof. In some cases, the one or more pouches may extend around the entire perimeter of the mask. FIG. 12 shows such mask with a pouch 10 extending around the entire perimeter of the mask.

The mask body portion is generally comprised of layers of nonwoven fabrics. The following table indicates the features of each layer of a specific embodiment of the present invention (this particular embodiment comprises three functional layers). These features include functional advantages, production technology of the layers and medical requirements in view of the material that they are made of.

TABLE 1

| Layer | Functions | Filtration substrate production technology | Adaptation of the raw material to medical requirements |
| --- | --- | --- | --- |
| External Layer | 1. Coarse mechanical filtration<br>2. Protection against liquids penetration<br>3. Constructive | SB (Spunbond), CARDED | 1. Keeps its properties even in humid and wear situations<br>2. Low resistance |

TABLE 1-continued

| Layer | Functions | Filtration substrate production technology | Adaptation of the raw material to medical requirements |
|---|---|---|---|
| | support<br>4. High tear resistance<br>5. Protection of the delicate filtration fabric from dismantling<br>6. Prevention of contaminants falling from the inner layers | | |
| Middle Layer | 1. Fine particles filtration through mechanical mechanism or in combination with an electrostatic media | MB (Meltbond), Electrostatic MB, Nanofiber | 1.99% filtration efficiency against microbes and viruses<br>2. Low resistance |
| Inner layer | 1. Skin contact compatible<br>2. Soft and airy | SB, Carded, Wetlaid | 1. Hypoallergenic<br>2. Reduces sweat when in contact with the skin |

According to an embodiment, the total thickness of the mask is usually between 0.4 mm and 1.5 mm and preferably 0.8 mm.

The mask provides a high standard of filtering (N-99) through it, capable of filtering 99% of all particles larger than 0.3 microns. The mask of the present invention provides at least the minimal required filtering factor (FIT factor) of 100. As noted in the table of FIG. 10, the actual readings of an experimental test indicate much higher FIT factor results. The factor value is determined by measuring the results of experimenters in POTRACOUNT PRO PLUS 8038. The protocol test comprises measurements made during seven exercises: regular breathing, deep breathing, while moving the head to the sides, while moving the head up and down, while reading a text aloud, leaning forward and regular breathing. Further details can be viewed in Table 2:

TABLE 2

| Measuring range of the Measuring instrument (Passing threshold = 100) | Protocol Test | Mask Type |
|---|---|---|
| 1-10,000+ | OSHA 29 CFR1910.134 | N99 |

The mask is adapted to easily and comfortably be worn on the user and harnessed thereon. The speech volume is minimally lowered when passed through the mask. The mask enables the user to have a maximal field of vision. The mask is compatible for use with eye-glasses and other medical instruments or protective appliances (e.g. a visor).

According to another aspect of the invention, the face mask body portion is further characterized by being folded into a series of pleats. The pleats provide flexibility to the mask, thus preventing a breakthrough of the sealing when speaking and when making other facial movements. Also, with the pleats, the surface area of the mask increases thus the total resistance of the mask (to breathing) decreases thus making it easier for the user to breath, without affecting the mask sealing. Accordingly, the filtering ability increases.

The pleats are made by folding the mask body portion into pleat layers and welding the edges together. According to one embodiment of the present invention the pleats are formed along the width of the mask and have a width usually between 17 cm and 25 cm, preferably 21 cm. The height of each pleat is usually between 2 cm and 5 cm, preferably 3.5 cm.

FIG. 6 shows an example of the mask with the pleats. The arrow 9 on the right side exemplifies the flexibility of the mask, the direction of the stretching of the mask during speech or during other facial movements, without affecting the sealing of the mask.

The suction of air also through the pleats, which increase the surface area through which air is forced through, decreases the resistance to breathing in relation to masks without pleats. In some cases the total filtering surface through which air flows through the mask is increased by 50-70%, compared to the mask design with no pleats. The air passing through the mask passes along a larger surface total, which causes the decrease in resistance. Similarly, the filtering ability increases due to the expansion of the total filtering surface. The reduction of the resistance to breathing is very significant to one wearing a mask for a long period of time.

According to another aspect of the invention, the face mask further comprises a single adjustable elastic strap for fitting said mask to the head and face of the user. The harnessing/fitting mechanism (shown in FIGS. 7a-7b) comprises one unified elastic strap threaded into wide channels 11 located on the sides of the mask. The threading creates two tightening strap loops 13 and 14 for fastening, one loop (13) adapted to be placed in the rear of the neck and the other loop (14) adapted to be placed in the rear of the head. A tightening buckle 15 is placed at an edge of the strap designed to improve fastening and adjusting the mask to the user. The tightening buckle 15 can be of any type of buckle known in the art (e.g. snap/gripping buckle) configured to release/hold the straps at a required length (point location of the straps). The buckle is manually shifted from the holding mode to the releasing mode to enable the straps to be tightened therethrough. Accordingly the buckle is manually shifted (or released from the former position) from the releasing mode to the holding mode to enable the straps to be held at the required length (preventing them from moving therethrough). This strapping feature allows a user to manually and personally control and tight fit of the mask to his own face, thus further ensuring the achievement of a tight seal and proper functioning of the mask.

Having a structure of two-way stretch (neck and head) and wide channels at the sides ensures uniform pressure on the neck and head, as well as a more efficient peripheral seal.

According to an embodiment of the present invention the elastic strap comprises rubber. The length of the strap is usually between 80 cm and 130 cm, preferably 105 cm. The width of the strap is usually between 0.8 cm and 1.2 cm, preferably 1 cm. The weight of the strap is usually between 5.4 gram/meter and 6 gram/meter, preferably 5.7 gram/meter. The strap can generally stretch between 120% and 150% of its original length. According to an embodiment, the strap comprises 70% Polyester and 30% Lycra. The buckle 15 is comprised of plastic. Optionally, a pad 16 is added to loop 13 for comfort.

Figure 8:
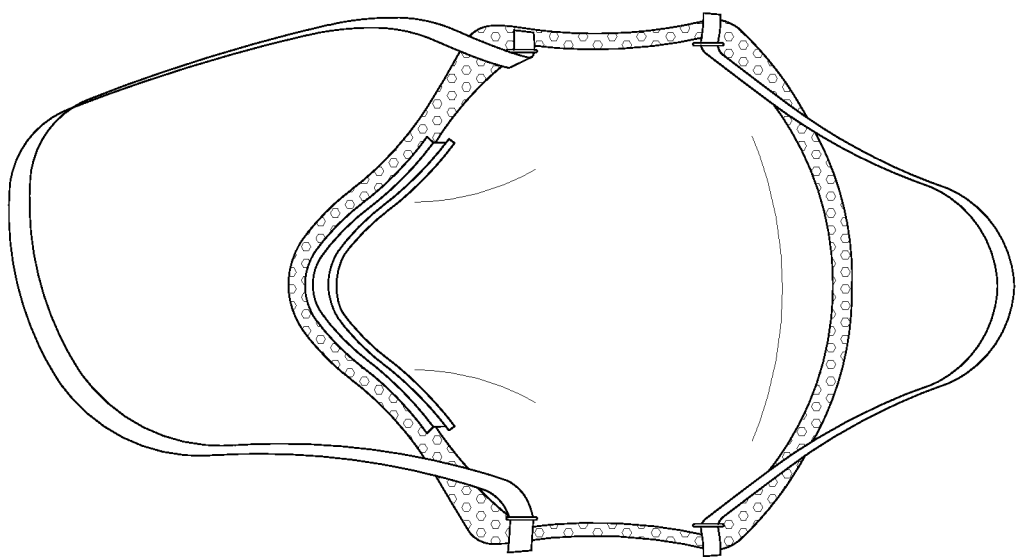
FIG. 8 illustrates a prior art mask.

The mask with one strap has a substantial advantage in relation to prior art masks. The even tension in all areas of the unified strap assists in the sealing of the mask. Prior art masks comprising more than one strap are attached to the mask by welding or stapling, cause pressure points at the attachment locations when pulled, and can burst the peripheral sealing of the mask. An example of the front and rear side of such prior art mask can be seen in FIG. 8. Prior art masks straps made of homogeneous non-woven material, such as latex free, have a tendency to lose flexibility after being maximally stretched. The present invention strap flexible material and the fact that the present invention strap is not stapled to the mask edges, but is a whole unified strap assists in preventing the strap from tearing and assists in preventing the breaking off of other mask portions.

Figure 9:
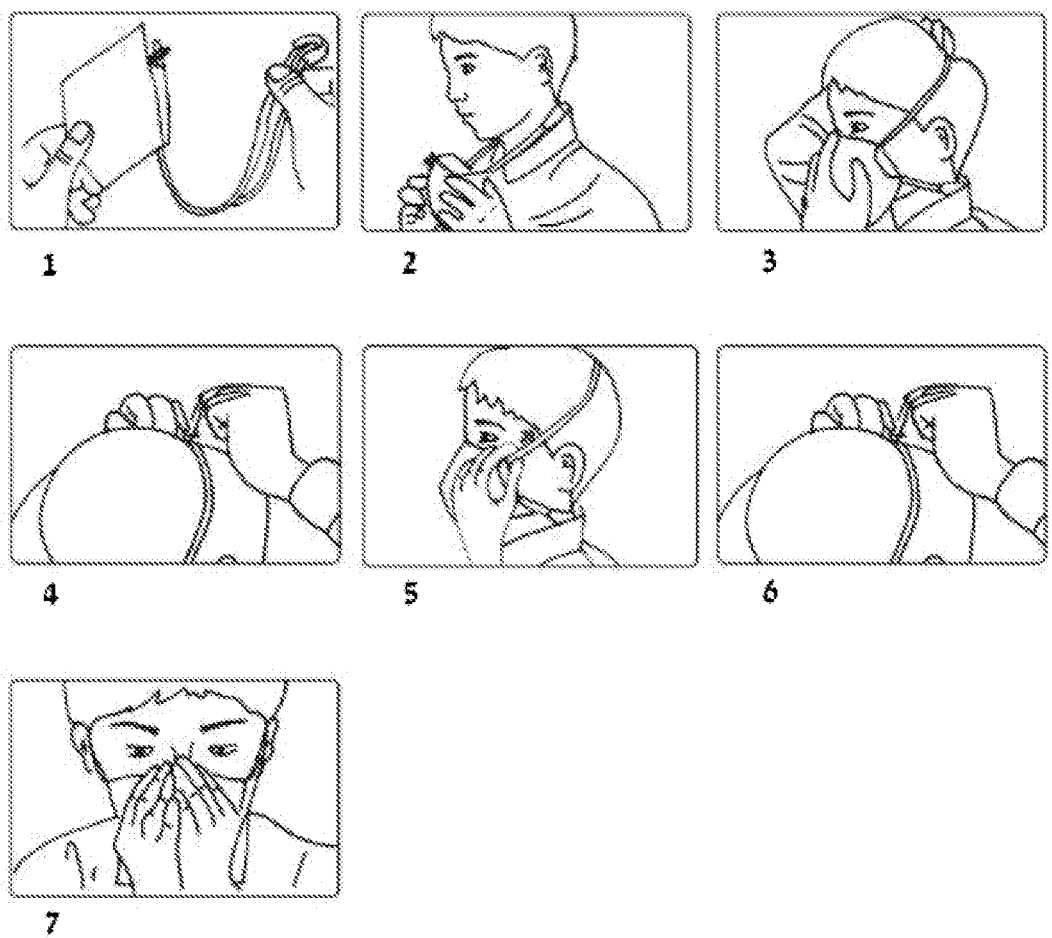
FIG. 9 illustrates an example of a user applying the mask with one strap on him, step by step.

FIG. 9 shows an example of a user applying the mask with one strap on him, step by step.

Step 1: The user holds the lower portion of the strap (the portion beneath channels 11 shown in FIG. 7a) in one hand and the mask in the other. The user pulls the loop adapted to be applied on the neck all the way until the buckle touches the mask channels 11.

Step 2: The user puts the lower portion of the strap such that it surrounds the rear end of the neck.

Step 3: The user puts the mask on his face, and pulls the buckle thus creating the top loop and puts the top loop around the top of his head.

Step 4: The user pulls and tightens the strap using the buckle which holds the strap at the required length.

Step 5: The user moves loose portions of the lower strap loop to the top strap loop such that the sealing of the mask is completed.

Step 6: The user again pulls and tightens the upper portion of the strap using the buckle which holds the strap at the required length.

Step 7: The user checks the sealing. If the mask is not sealed the used slightly repositions the mask such that the cushions are centered at the bridge of the nose, causing a complete sealing.

Figure 13:
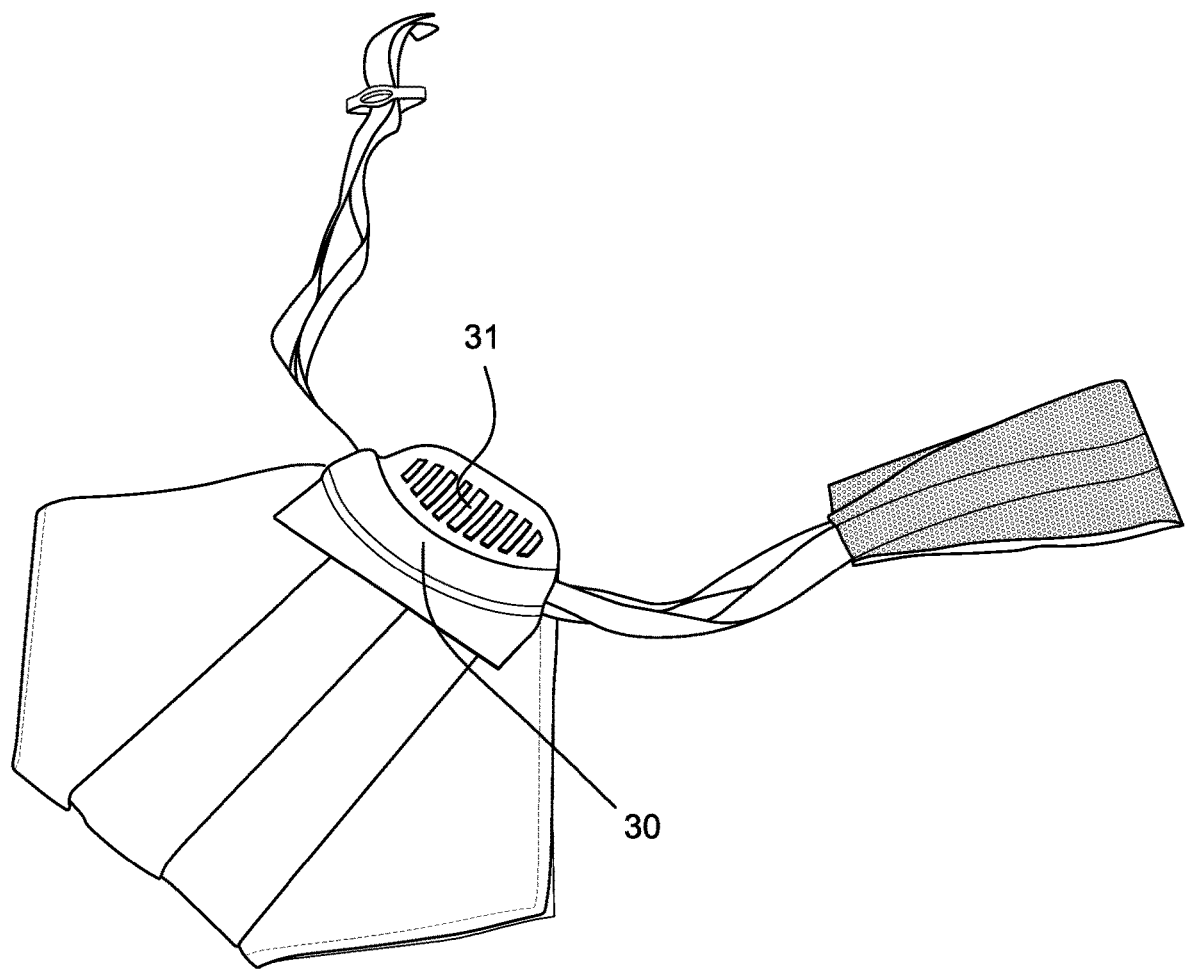
FIGS. 13 and 14 illustrate an embodiment of the present invention wherein the mask comprises a threading channel attached to a grip tab at each of the side edges of the mask.

According to an embodiment of the present invention, the mask comprises a threading channel 30 attached to a grip tab 31, at each of the side edges of the mask, (see folded mask in FIG. 13). The threading channels 30 enables a smooth freely passage of the mask strap therethrough. The grip tabs 31 assists the user to correctly symmetrically place and stabilize the mask on the face. Optionally, each threading channel 30 and grip tab 31 are made by plastic injection and are welded to the front and back sides of each of the side edges of the mask. Alternatively, the threading channels and grip tabs could be made of a nonwoven fabric. The threading channel 30 cross section either is round or has a polygon shape. The threading channel 30 length is usually 5 cm-7 cm, preferably 6 cm, and its width is usually 2 cm-5 cm, preferably 3 cm.

Figure 14:
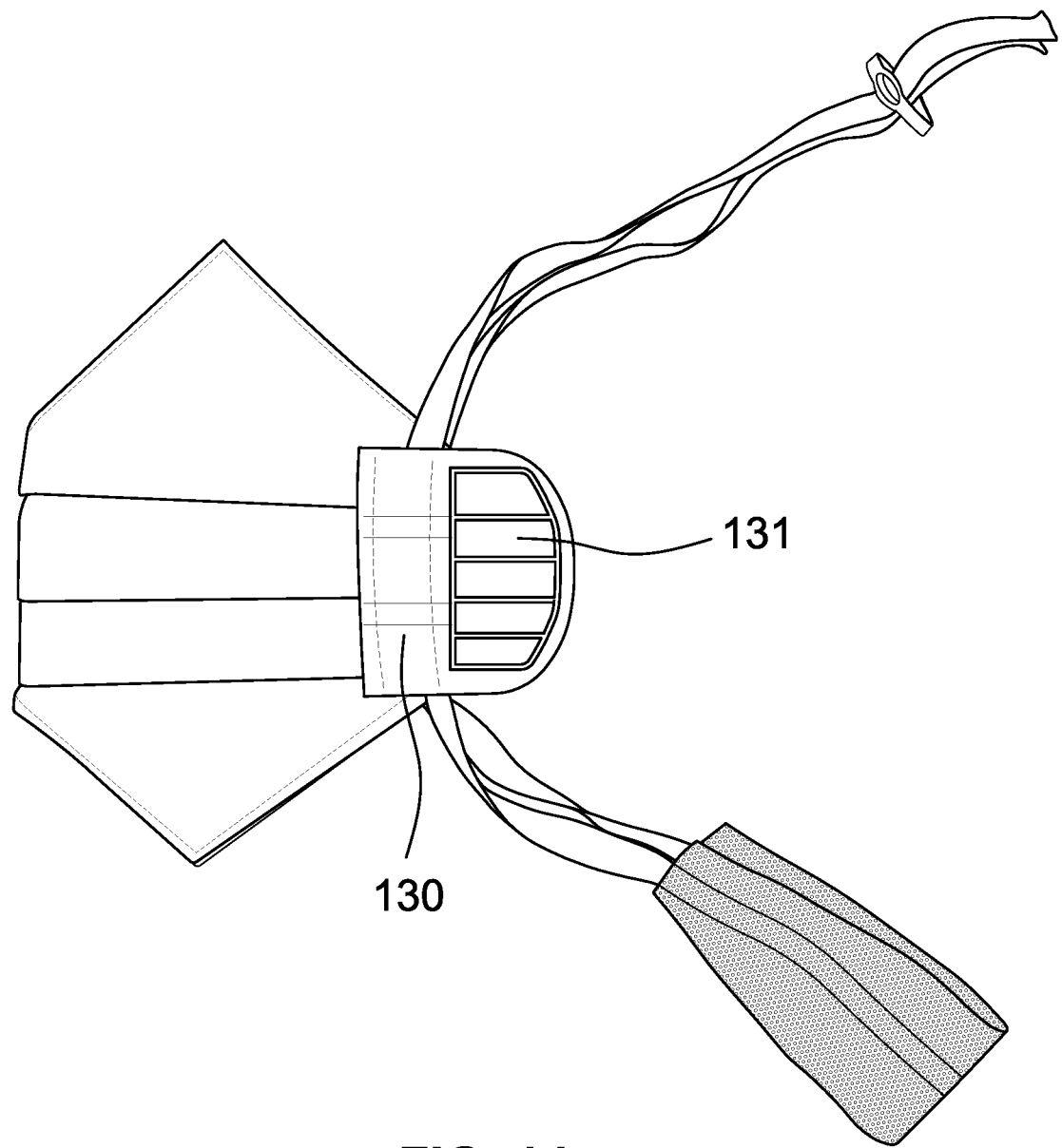

FIG. 14 shows this embodiment wherein each threading channel 130 and grip tab 131 are made of the same material that the mask is made of and is an integral part of the mask body. The threading channel 130 and grip tab 131 portions are welded to be stiffened and hardened.

Example 1

The present invention mask filtration/transferability of particles has been tested on several subjects. The test results of the present invention mask were very good indicating high and very efficient capabilities for filtration of biological agents.

FIG. 10 illustrates the test results of an experiment applied on 2 mask models of the present invention and 3 prior art mask products. All of the masks were tested on all of the experimental human subjects.

The air was tested at both (inner and outer) sides of the mask and the appropriate FIT factor was calculated accordingly, as known in the art, wherein FIT factor 100 indicates a passing grade according to international standard. All of the experiments on the present invention models passed. The best result was of the pleated model which gave a result factor of 798, wherein factor 1000 is of that of a standard chemical, biological, radiological, nuclear (CBRN) gas mask.

Example 2

FIG. 11 illustrates a graph of the test results of the breathing resistance of 2 mask models of the present invention (one with the pleats, the other—flat cut, without pleats) and a Prior Art shelf mask product. All of the masks were tested on a human head manikin. The resistance of the masks is calculated by finding the difference of air pressure between a calculation of the air pressure during a flow of air not passing through a mask and a calculation of the air pressure with the same flow of air passing through a mask.

The following table indicates the European standard—EN 149:2001+A1, for the resistance of the masks.

TABLE 3

|  | Constant flow (Liters per minute) | Maximal Resistance (mmH$_2$O) | Maximal Penetration |
| --- | --- | --- | --- |
| During intake | 30 | 10 | — |
|  | 95 | 30 | 1% for Aerosols NaCl and DOP |
| During outtake | 160 | 30 | — |

The following table indicates the US standard NIOSH: 42 CFR PART 84 Subpart k, for the resistance of the masks.

TABLE 4

|  | Constant flow (Liters per minute) | Maximal Resistance (mmH$_2$O) | Maximal Penetration |
| --- | --- | --- | --- |
| During intake | 85 | 35 | 1% for Aerosols NaCl and DOP |
| During outtake | — | 25 | — |

These table values can also be viewed on the graphs of FIG. 11.

Figure 15:
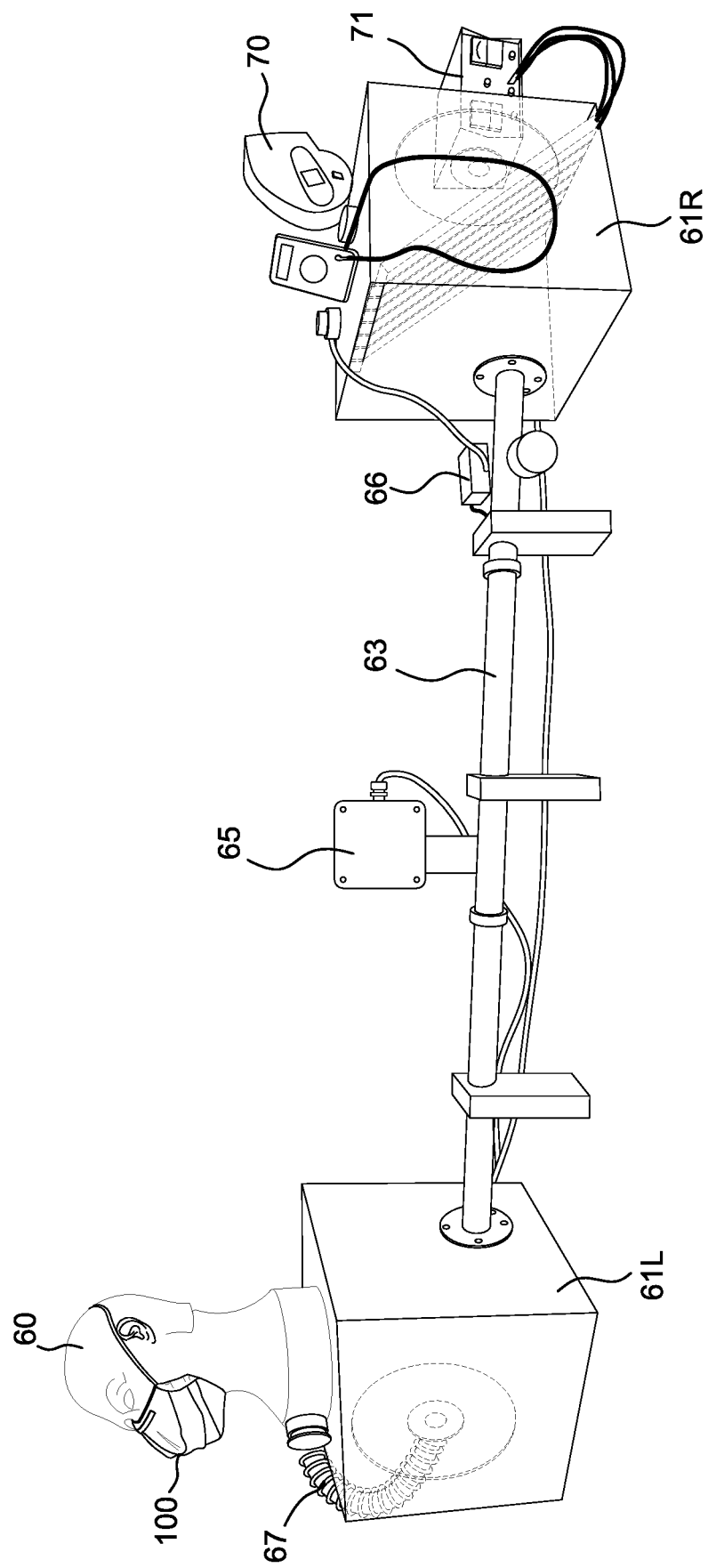
FIGS. 15 and 16 illustrate the components of an experiment done with the present invention.

FIG. 15 illustrates an example of an experimental set up of the mask resistance testing, wherein the results can be seen in the graphs of FIG. 11. A mask 100 was applied on the face of a manikin 60. An air generator (blower) 70 was attached to one end of an air flow line (on the right). Power source generator 71 supplied power to air generator 70. The other end of the air flow line (on the left) was connected to the nostrils of the head manikin 60. Two transparent cubic cells 61R, 61L, each with a 40 cm side length, and a stainless steel tube 63 therebetween, are part of the air flow line. The left transparent cubic cell 61L was coupled by a tube 67 to the manikin 60, and the air generator 70 was coupled to transparent cubic cells 61R. A flow meter 65 was connected to tube 63 and adapted to measure the air flow therethrough. The flow meter 65 is of Model No. FT-24 510 of KURTZ instruments Inc. is capable of measuring up to 300 Liters per Minute. A pressure transducer 66 was connected to tube 63 and adapted to measure the air pressure therein. The pressure transducer 66 is of Model No. B223 of MSK USA, has a range of measuring up to 10 Torr.

The cubic cells 61L, 61R dimensions, ensured a linear air flow and a minimal pressure drop along the air flow line. The tube 63 diameter and the usage of the "HOT WIRE" type flow meter 65 ensure a minimal pressure drop along tube 63. The air flow system was built according to the German standard—Din 24163.

Figure 16:
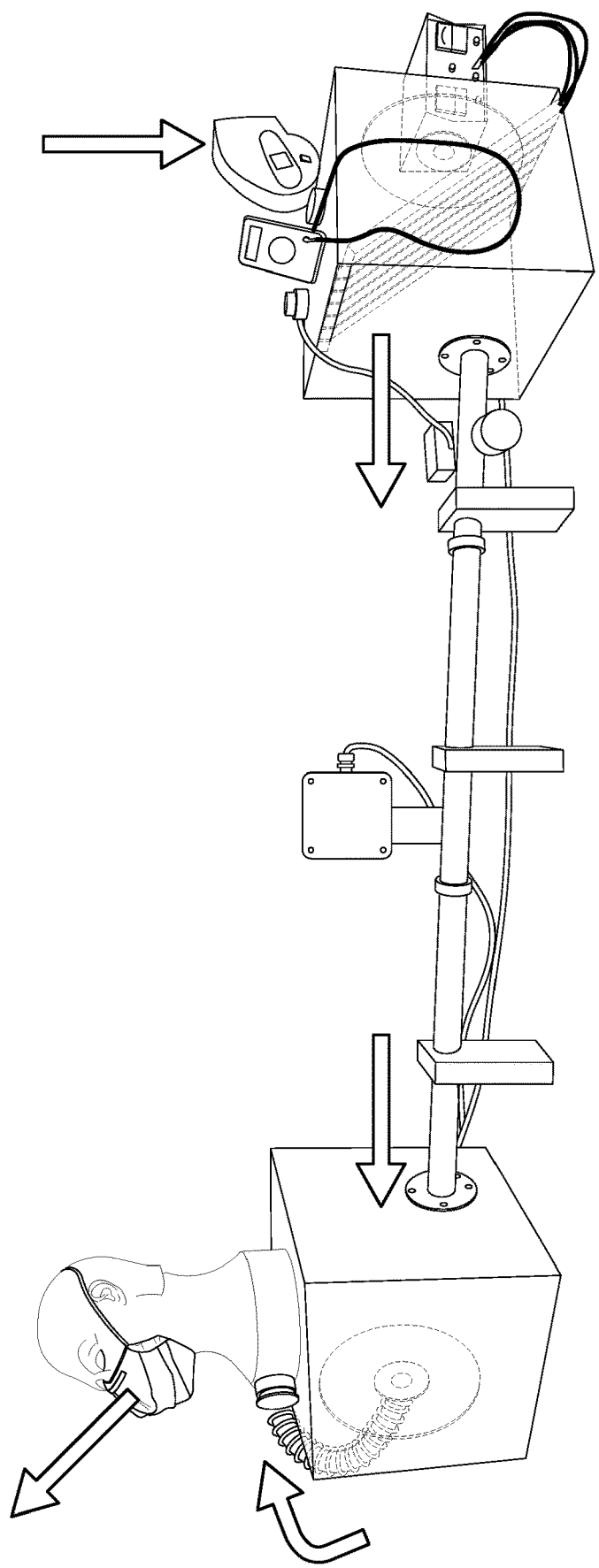

The experiment was carried out in a manner resembling an outtake of air (OUTLET air flow), i.e. the air generator 70 sucked air into the right cubic cell 61R, the air in the system traveled leftwards through the stainless steel tube 63, into the left cubic cell 61L, to tube 67 to the manikin 60, out of the nostrils through the mask out of the air flow line. FIG. 16 shows (by arrows) the direction of air flow of the experiment.

The experiment was carried out at different air flow rates—80, 120, 160, 200 (Liters/Minute), as shown on the top graph of FIG. 11. The system air pressure was measured by the pressure transducer 66 once with a specific mask and once without the mask. The difference of a measurement of air pressure between both of said instances (with/without mask) give the required resistance (in in units of pressure—mmH$_2$O).

The experiment was also carried out in a manner resembling an intake of air (not shown). The head manikin 60 with the mask 100 on it was switched with the air generator 70, such that the air generator 70 was connected to tube 67 applying a negative pressure (suction from within the air line), thus the air in the air line also traveled leftwards. The head manikin 60 was coupled to right cubic cell 61R, thus the air entered the air line through the mask into the nostrils and into right cubic cell 61R. From there the air in the system traveled leftwards through the stainless steel tube 63, into the left cubic cell 61L, to tube 67 to the air generator 70 and out of the air flow line.

The experiment was carried out at different air flow rates—30, 60, 90, 120, 150 (Liters/Minute), as shown on the bottom graph of FIG. 11. The system air pressure was measured by the pressure transducer 66 once with a specific mask and once without the mask. The difference of a measurement of air pressure between both of said instances (with/without mask) give the required resistance (in in units of pressure—mmH$_2$O).

As said, the experiment was carried out three times, once when mask 100 used was a prior art mask, once when the mask 100 used was the present invention flat cut model and once when the mask 100 used was the present invention pleats model. The analysis of the experiment provides clear results, wherein the present invention masks comprise a low resistance in comparison with the prior art mask. Also, the present invention masks comprise a much lower resistance than that of the standard US and EP requirements.

While some of the embodiments of the invention have been described by way of illustration, it will be apparent that the invention can be carried into practice with many modifications, variations and adaptations, and with the use of numerous equivalents or alternative solutions that are within the scope of a person skilled in the art, without departing from the spirit of the invention, or the scope of the claims.

The invention claimed is:

1. A face mask comprising:
    (a) a mask body portion configured to surround a mouth and at least part of a nose of a wearer; and
    (b) a sealed compressible cushion attached to an inner proximal side of said mask body portion such that, when in use, the sealed compressible cushion is configured to be in contact with the wearer's face, wherein a middle portion of said sealed compressible cushion is placed in close proximity to a middle portion of the superior perimeter of said mask body portion, and wherein said sealed compressible cushion is partially filled with a fluid; wherein said sealed compressible cushion is completely sealed,
    wherein the sealed compressible cushion comprises two lateral pocket portions, wherein said two lateral pocket portions have larger volumes than that of the middle portion of said sealed compressible cushion, wherein the middle portion of said sealed compressible cushion is configured to fit on a bridge of the nose of the wearer, and said two lateral pocket portions are configured to be deployed on the sides of the nose of the wearer,
    wherein part of the fluid in one lateral pocket portion is configured to travel to the other lateral pocket portion;
    thus said sealed compressible cushion being configured to seal areas between an upper cheek and an eye socket of the wearer, and
    wherein the sealed compressible cushion does not include a valve, such that fluid cannot be added to or removed from the sealed compressible cushion.

2. The face mask according to claim 1, wherein the sealed compressible cushion is comprised of two EVA (Ethylene-vinyl acetate) films.

3. The face mask according to claim 1, wherein the sealed compressible cushion is comprised of Polyethylene (PE) films.

4. The face mask according to claim 1, wherein the sealed compressible cushion is comprised of a laminate comprising Polyethylene (PE).

5. The face mask according to claim 1, wherein the sealed compressible cushion is attached to the mask body portion and wherein the middle portion of said sealed compressible cushion is attached at close proximity to the middle portion of the superior perimeter of said mask body portion.

6. The face mask according to claim 1, wherein the mask body portion further comprises a holding element attached to the inner face of said mask body portion at close proximity to the middle portion of the superior perimeter of said mask body portion; wherein said holding element is configured to receive and hold a portion of the sealed compressible cushion threaded thereinto.

7. The face mask according to claim 1, wherein the sealed compressible cushion is comprised of films or sheets having a shape of two adjacent polygons having a common portion in the middle portion of said sealed compressible cushion.

8. The face mask according to claim 7, wherein the two adjacent polygons are trapezoids.

9. The face mask according to claim 1, wherein the mask body portion is comprised of layers of nonwoven fabrics.

10. The face mask according to claim 9, wherein the mask body portion comprises three functional layers.

11. The face mask according to claim 1, wherein the mask body portion comprises a portion that is folded into a series of pleats.

12. The face mask according to claim 11, wherein the series of pleats are formed along a width portion of the mask body portion and are made by folding a portion of the mask body portion into pleat layers and welding edges of said pleat layers together.

13. A face mask according to claim 1, wherein the cushion is a single compartment.

* * * * *